(12) United States Patent
Sikander et al.

(10) Patent No.: US 12,087,452 B2
(45) Date of Patent: Sep. 10, 2024

(54) SYSTEM AND METHOD TO REGULARIZE CANCER TREATMENT DATA FOR SYSTEMATIC RECORDING

(71) Applicant: IQVIA Inc., Parsippany, NJ (US)

(72) Inventors: Sanam Sikander, London (GB); Edmund Drage, London (GB)

(73) Assignee: IQVIA Inc., Parsippany, NJ (US)

( * ) Notice: Subject to any disclaimer, the term of this patent is extended or adjusted under 35 U.S.C. 154(b) by 0 days.

(21) Appl. No.: 17/990,827

(22) Filed: Nov. 21, 2022

(65) Prior Publication Data

US 2023/0085204 A1   Mar. 16, 2023

Related U.S. Application Data

(63) Continuation of application No. 17/074,240, filed on Oct. 19, 2020, now Pat. No. 11,538,594, which is a
(Continued)

(51) Int. Cl.
*G06F 16/25* (2019.01)
*G16H 20/10* (2018.01)
(Continued)

(52) U.S. Cl.
CPC ........... *G16H 70/20* (2018.01); *G06F 16/258* (2019.01); *G16H 20/10* (2018.01); *G16H 50/70* (2018.01)

(58) Field of Classification Search
CPC ........ G16H 70/20; G16H 20/10; G16H 50/70; G06F 16/258
(Continued)

(56) References Cited

U.S. PATENT DOCUMENTS 8,200,509 B2   6/2012 Kenedy et al.
10,811,142 B2   10/2020 Sikander et al.
(Continued)

OTHER PUBLICATIONS

Chemodataset.nhs.uk [online], "Systemic Anti-Cancer Therapy: An introduction to Chemotherapy and SACT," Apr. 11, 2017, retrieved on May 26, 2023, retrieved from URL<www.chemodataset.nhs.uk/view?rid=149>, 83 pages.
(Continued)

*Primary Examiner* — Michael Pham
(74) *Attorney, Agent, or Firm* — Fish & Richardson P.C.

(57) ABSTRACT

Implementations provide a method to consolidate data records of regimens for treating oncology conditions. The method includes: accessing data records each encoding multi-tier data characteristics of a regimen for treating a particular oncology condition; receiving a first data record encoding a first regimen specific to a first healthcare provider institution; parsing the first data record according to a hierarchy of the encoded multi-tier data characteristics; distributing a respective weight to each of the encoded data characteristics to account for the potentially missing data characteristic; comparing data characteristics of the first data record with data characteristics from the data records by applying the respective weight to each data characteristic at a particular tier of the hierarchy such that a respective compound score is generated for each data record; and based on the compound scores for all data records, determining a prevailing data record of regimen as matching the first data record.

20 Claims, 4 Drawing Sheets

Related U.S. Application Data continuation of application No. 15/904,793, filed on Feb. 26, 2018, now Pat. No. 10,811,142.

(51) Int. Cl.
*G16H 70/20* (2018.01)
*G16H 50/70* (2018.01)

(58) Field of Classification Search
USPC .......................................................... 707/811
See application file for complete search history.

(56) References Cited

U.S. PATENT DOCUMENTS

| | | | |
|---|---|---|---|
| 11,538,594 | B2 | 12/2022 | Sikander et al. |
| 2006/0058966 | A1 | 3/2006 | Bruckner |
| 2014/0316797 | A1 | 10/2014 | Biernacki |
| 2015/0339442 | A1* | 11/2015 | Oleynik ............... G16H 50/70 705/3 |
| 2019/0233895 | A1 | 8/2019 | Kurzrock et al. |
| 2019/0267143 | A1 | 8/2019 | Sikander et al. |
| 2021/0090751 | A1 | 3/2021 | Sikander et al. |
| 2023/0085204 | A1 | 3/2023 | Sikander et al. |

OTHER PUBLICATIONS

Ex Parte Samuel S. Adams, Robert R. Friedlander, James R. Kraemer, and Jeb R. Linton, Patent Trial and Appeal Board, Patent and Trademark Office (P.T.O.), Appeal 2017-005528, U.S. Appl. No. 13/733,066, 2017 WL 4711670 (Patent Tr. & App. Bd.), Sep. 18, 2017, 7 pages.

Extended European Search Report and Written Opinion in Appln. No. 19159360, dated Oct. 14, 2019, 9 pages.

Gurney et al., "How to calculate the dose of chemotherapy," Br J Cancer, Apr. 22, 2002, 86(8): 1297-1302.

International Statistical Classification of Diseases and Related Health Problems: 10th Revision (ICD-10), Dec. 7, 2015, 2131 pages (abstract only).

Londoncanceralliance.nhs.uk [online], "Generic Chemotherapy Protocol Guidelines," available on or before Aug. 3, 2016, via Internet Archive: Wayback Machine URL<https://web.archive.org/web/20160803231716/http://www.londoncanceralliance.nhs.uk/media/56148/SELCN_Generic%20Chemo_Guidelines%20April%202013.pdf>, retrieved on May 26, 2023, URL<http://www.londoncanceralliance.nhs.uk/media/56148/SELCN_Generic%20Chemo_Guidelines%20April%202013.pdf>, 8 pages.

Nccn.org [online], "About the NCCN Clinical Practice Guidelines in Oncology (NCCN Guidelines®)," available on or before Jun. 3, 2017, via Internet Archive: Wayback Machine URL<https://web.archive.org/web/20170206204442/https://www.nccn.org/professionals/default.aspx>, retrieved on May 26, 2023, URL<https://www.nccn.org/professionals/default.aspx>, 2 pages.

Oncologynurseadvisor.com [online], "Cancer Treatment Regimens," available on or before Oct. 19, 2017, via Internet Archive: Wayback Machine URL<https://web.archive.org/web/20170927041135/http://www.oncologynurseadvisor.com/chemotherapy-regimens/section/2171/>, retrieved on May 26, 2023, URL<http://www.oncologynurseadvisor.com/chemotherapy-regimens/section/2171/>, 4 pages.

*Secured Mail Solutions LLC*, Plaintiff-Appellant v. *Universal Wilde, Inc.*, Defendant-Appellee, 2016-1728, United States Court of Appeals for the Federal Circuit, Appeal from the United States District Court for the Central District of California in No. 2:15-cv-07562-DOCGJS, Judge David O. Carter, Decided Oct. 16, 2017, 14 pages.

Shah et al., "The relevance of drug sequence in combination chemotherapy," Drug Resist Update, Dec. 2000, 3(6):335-356 (abstract only).

Stat.cmu.edu [online], "Statistical Methods for Eliciting Probability Distributions," Jan. 4, 2005, retrieved on May 26, 2023, retrieved from URL<https://www.stat.cmu.edu/tr/tr808/tr808.pdf>, 74 pages.

Syed et al., "Vector Space Models for Encoding and Retrieving Longitudinal Medical Record Data," LNCS, 2016, 9579:3-15.

* cited by examiner

SYSTEM AND METHOD TO REGULARIZE CANCER TREATMENT DATA FOR SYSTEMATIC RECORDING

CROSS REFERENCE TO RELATED APPLICATIONS

This application claims benefit of U.S. patent application Ser. No. 17/074,240, filed Oct. 19, 2020, which is a continuation of U.S. patent application Ser. No. 15/904,793, filed Feb. 26, 2018, now U.S. Pat. No. 10,811,142, which is hereby incorporated by reference in its entirely.

BACKGROUND

Cancer treatment data are reported and recorded from databases of various healthcare providers.

TECHNICAL FIELD

This disclosure relates to normalizing irregular cancer treatment data for systematic and large-scale recording to facilitate standardized analysis of cancer treatment.

SUMMARY

In one aspect, some implementations provide a computer-implemented method to consolidate data records of regimens for treating oncology conditions as reported from multiple healthcare provider institutions. The method includes: accessing data records stored at a central data server, each data record encoding multi-tier data characteristics of a regimen for treating a particular oncology condition; receiving, from a first data server managed by a first healthcare provider institution, a first data record encoding a first regimen for treating the particular oncology condition, the first regimen being specific to the first healthcare provider institution; parsing the first data record according to a hierarchy of the encoded multi-tier data characteristics; in response to determining that a particular encoded data characteristic at a particular tier of the hierarchy is absent from the first data record, flagging the particular encoded data characteristic as potentially missing in the first data record; distributing a respective weight to each of the encoded data characteristics to account for the potentially missing data characteristic; comparing data characteristics of the first data record with data characteristics from the data records stored at the central data server by applying the respective weight to each data characteristic at a particular tier of the hierarchy such that a respective compound score is generated to indicate a degree of match for each data record of regimens stored at the central data server; and based on the compound scores for all data records of regimens stored at the central server, determining a prevailing data record of regimen stored at the central server as matching the first data record received from the first healthcare provider institution such that when a data record encoding the first regimen is received later, the prevailing data record of regimen is presented without duplicating the comparison to generate the respective compound scores that indicate the degrees of match for stored data records of regimens.

Implementations may include one or more of the following features.

The method may further include: receiving, from a second data server managed by a second healthcare provider institution that is different from the first healthcare provider institution, a second data record encoding the second regimen for treating the particular oncology condition, the second regimen being specific to the second healthcare provider institution; parsing the second data record according to the hierarchy of the encoded multi-tier data characteristics; and in response to determining that the second regimen encoded by the second data record corresponds to the first regimen, presenting the prevailing data record of regimen without duplicating the comparison.

Determining the prevailing data record may include: in response to determining that the corresponding compound score for a particular data record encoding a particular regimen exceeds the remaining compound scores by a threshold value, choosing the particular data record as the prevailing data record.

Determining the prevailing data record may include: in response to determining that the corresponding compound scores for more than a threshold number of data records are within a particular margin, re-distributing a new respective weight to each of the encoded data characteristics in the hierarchy.

Comparing data characteristics of the first data record with data characteristics from the data records stored at the central data server may include: comparing data characteristics of administering a cocktail of multiple drugs as encoded by the first data record with data characteristics from the data records that include the multiple drugs.

Comparing data characteristics of the first data record with data characteristics from the data records stored at the central data server may include: comparing data characteristics of multiple administrations involving a cocktail of multiple drugs as encoded by the first data record with data characteristics from the data records that include the multiple drugs.

Comparing data characteristics of the first data record with data characteristics from the data records stored at the central data server may include: comparing data characteristics of administering a brand name drug as encoded by the first data record with data characteristics from the data records that include the brand name drug based on a matching standard that is higher than that of a generic drug.

Accessing data records each encoding a multi-tier data characteristics of a regimen for treating a particular oncology condition may include: accessing a data object representing a first tier of information encoding a cocktail combination of drugs for treating the particular oncology condition, a second tier of information encoding cycles for each drug from the cocktail combination of the first tier for treating the particular oncology condition, and a third tier of information encoding administration details of administering each drug from the cocktail combination of the first tier during cycles from the second tier. The compound score may be generated by combining contributions from data characteristics at all three tiers. The data object may encode data characteristics on an ladder of importance, and wherein combining contributions from data characteristics at all three tiers may include: applying the respective weight to each of the encoded data characteristics by allocating more weight at levels that are higher in the hierarchy, and less weight to the potentially missing data characteristics.

In another aspect, some implementations provide a computer system comprising one or more processors configured to perform the operations of: accessing data records stored at a central data server, each data record encoding multi-tier data characteristics of a regimen for treating a particular oncology condition; receiving, from a first data server managed by a first healthcare provider institution, a first data record encoding a first regimen for treating the particular oncology condition, the first regimen being specific to the first healthcare provider institution; parsing the first data record according to a hierarchy of the encoded multi-tier data characteristics; in response to determining that a particular encoded data characteristic at a particular tier of the hierarchy is absent from the first data record, flagging the particular encoded data characteristic as potentially missing in the first data record; distributing a respective weight to each of the encoded data characteristics to account for the potentially missing data characteristic; comparing data characteristics of the first data record with data characteristics from the data records stored at the central data server by applying the respective weight to each data characteristic at a particular tier of the hierarchy such that a respective compound score is generated to indicate a degree of match for each data record of regimens stored at the central data server; and based on the compound scores for all data records of regimens stored at the central server, determining a prevailing data record of regimen stored at the central server as matching the first data record received from the first healthcare provider institution such that when a data record encoding the first regimen is received later, the prevailing data record of regimen is presented without duplicating the comparison to generate the respective compound scores that indicate the degrees of match for stored data records of regimens.

Implementations may include one or more of the following features.

The operations may further include: receiving, from a second data server managed by a second healthcare provider institution that is different from the first healthcare provider institution, a second data record encoding the second regimen for treating the particular oncology condition, the second regimen being specific to the second healthcare provider institution; parsing the second data record according to the hierarchy of the encoded multi-tier data characteristics; and in response to determining that the second regimen encoded by the second data record corresponds to the first regimen, presenting the prevailing data record of regimen without duplicating the comparison.

The operations may further include: in response to determining that the corresponding compound score for a particular data record encoding a particular regimen exceeds the remaining compound scores by a threshold value, choosing the particular data record as the prevailing data record.

Determining the prevailing data record may include: in response to determining that the corresponding compound scores for more than a threshold number of data records are within a particular margin, re-distributing a new respective weight to each of the encoded data characteristics in the hierarchy.

Comparing data characteristics of the first data record with data characteristics from the data records stored at the central data server may include: comparing data characteristics of administering a cocktail of multiple drugs as encoded by the first data record with data characteristics from the data records that include the multiple drugs.

Comparing data characteristics of the first data record with data characteristics from the data records stored at the central data server may include: comparing data characteristics of multiple administrations involving a cocktail of multiple drugs as encoded by the first data record with data characteristics from the data records that include the multiple drugs.

Comparing data characteristics of the first data record with data characteristics from the data records stored at the central data server may include: comparing data characteristics of administering a brand name drug as encoded by the first data record with data characteristics from the data records that include the brand name drug based on a matching standard that is higher than that of a generic drug.

Accessing data records each encoding a multi-tier data characteristics of a regimen for treating a particular oncology condition may include: accessing a data object representing a first tier of information encoding a cocktail combination of drugs for treating the particular oncology condition, a second tier of information encoding cycles for each drug from the cocktail combination of the first tier for treating the particular oncology condition, and a third tier of information encoding administration details of administering each drug from the cocktail combination of the first tier during cycles from the second tier.

The compound score may be generated by combining contributions from data characteristics at all three tiers. The data object may encode data characteristics on an ladder of importance, and wherein combining contributions from data characteristics at all three tiers may include: applying the respective weight to each of the encoded data characteristics by allocating more weight at levels that are higher in the hierarchy, and less weight to the potentially missing data characteristics.

Implementations of the above techniques include a method, computer program product and a system. The computer program product is suitably embodied in a non-transitory machine-readable medium and includes instructions executable by one or more processors. The instructions are configured to cause the one or more processors to perform the above described actions.

The system includes one or more processors and instructions embedded in a non-transitory machine-readable medium that are executable by the one or more processors. The instructions, when executed, are configured to cause the one or more processors to perform the above described actions. The default position is not to use any external databases, but the system could be configured to perform a database check if needed.

The details of one or more aspects of the subject matter described in this specification are set forth in the accompanying drawings and the description below. Other features, aspects, and advantages of the subject matter will become apparent from the description, the drawings, and the claims.

DETAILED DESCRIPTION

This disclosure generally describes systems and methods for normalizing irregular cancer treatment regimen data, often lodged in an ad-hoc manner. In oncology, a regimen refers to a prescribed course of treatment, in particular involving chemotherapy. Such a regimen defines the drugs to be used, their dosage, the frequency and duration of treatments, and other considerations. In modern oncology, many regimens combine several chemotherapy drugs in combination chemotherapy.

Noteworthy is that the majority of drugs used in cancer chemotherapy are cytostatic, many via cytotoxicity. A fundamental philosophy of medical oncology, including combination chemotherapy, is that different drugs work through different mechanisms, and that the results of using multiple drugs will be synergistic to some extent.

Because the drugs in combination have different dose-limiting adverse effects, judicious discretion must be exercised when giving the drugs together at full doses in chemotherapy regimens. Indeed, oncologists often painstakingly develop a "cocktail" that combines several drugs to treat a particular patient. In this context, today's systemic anti-cancer therapies and treatment regimens are increasingly complex. Such increase of complexity in new treatments has led to a concomitant increase in variability of collecting and collating information in oncology. As a result, there is a major gap in assessing which treatments of combination treatment are most efficacious or cost-effective for which types of patients (which cancer, which line of therapy) at what point in time. As the oncology pipelines experiences cycles of development and new treatments enter the market for single and multi-indications, new models for determining cost and efficacy of case-dependent combination treatment may be needed. Yet, the historic dearth of structured data and standardization in oncology treatment represents a major hindrance towards measured management.

Implementations disclosed herein can harmonize, standardize and interpret a heterogeneous pool of oncology treatment regimen data so that such information is parsed into a uniform and standardized database that stakeholders can use to glean insights on oncology treatment practice in the real world setting. Once the reported data is received from a participating healthcare provider, treatment regimen data is extracted, tokenized, pseudonymized and de-identified. Subsequently, the anonymized treatment regimen data will be transferred to a data warehouse. Implementations disclosed herein may select hospital reported data characteristics related to regimen treatment plans.

The implementations may use the combination of reported values and apply a series of calculations and filters to compare the reported treatment regimen against a consolidated list of guideline recommended regimens to identify the closest match between the institution (e.g., healthcare provider) derived and guideline reported regimen. Using this regimen matching approach, data captured from hospitals across different regions and under varying conventions can be consolidated to generate a uniform reporting output on the use of combination of pharmaceuticals by treatment regimens as well as common treatment practices. The implementations aim to provide comprehensive and contemporaneous data from different treating institutions on the actual use of anti-cancer medicines in clinical practice in a standardized manner designed for convenient interface for decision-makers to derive full value from these therapy regimens. Implementations may permit new models of access and supporting treatment choice for clinicians and patients.

Figure 1:
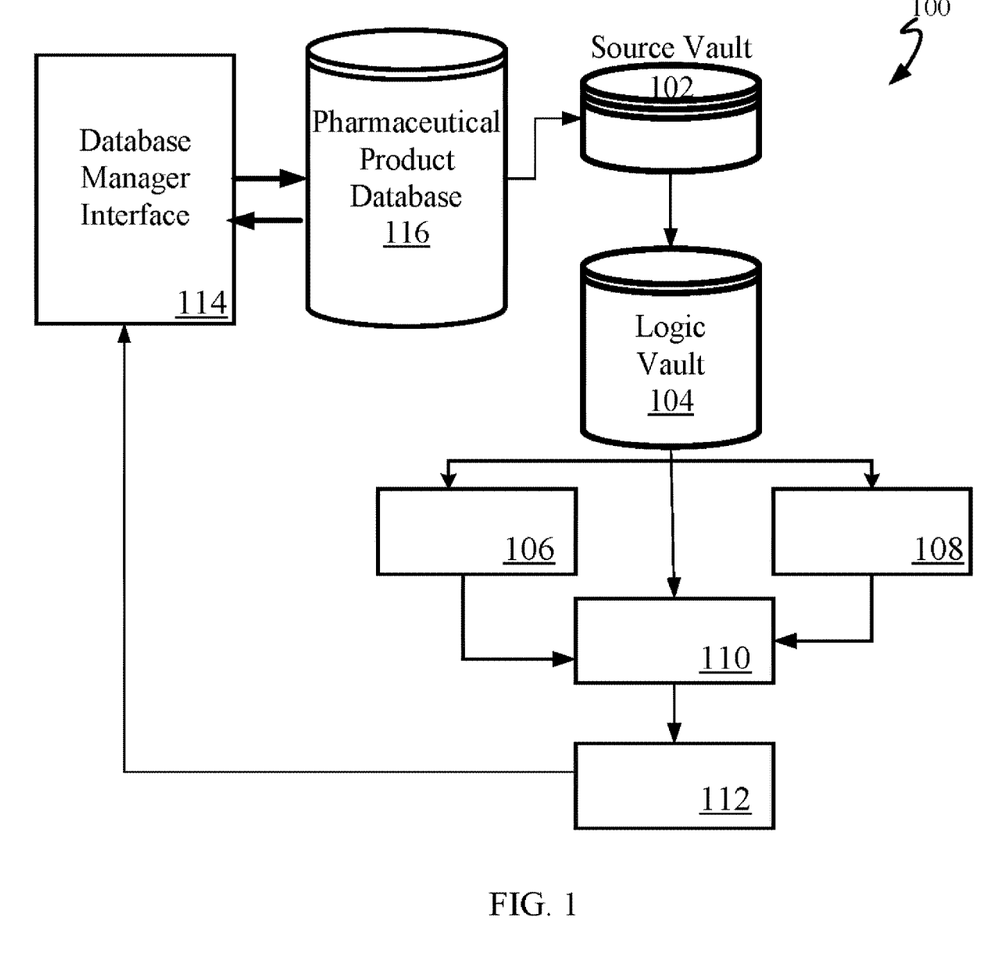
FIG. 1 shows an example of a network configuration to regularize cancer treatment data for systematic and large-scale recording to facilitate standardization of cancer treatment.

FIG. 1 shows an example of a network configuration 100 that is capable of normalizing irregular cancer treatment regimen data for systematic and large-scale recording to facilitate standardization of cancer treatment. Initially, treatment data for an oncology condition is reported from a participating healthcare provider institution, such as a cancer clinic, an oncology department of a hospital, or an oncology nursing facility. Once the reported data is received from a participating healthcare provider, treatment regimen data is extracted, tokenized, pseudonymized and de-identified. Subsequently, the anonymized treatment regimen data will be transferred to a data warehouse 102, which may also be known as a source vault. More details on such operations surrounding the source vault are laid out in step 202 of FIG. 2. Each reported regimen data stored in this vault are encoded at three hierarchical levels, namely, a level corresponding to regimen 302A at the top, a level corresponding to cycle 303 in the middle, and a level corresponding to administration 304 at the bottom, as delineated in FIG. 3. Each level contains data characteristics describing traits of the treatment regimen that combines several constituent pharmaceutical drugs for a particular patient whose identity has been concealed. Implementations disclosed herein may operate on various aspects of the data characteristics according to, for example, steps 204 to 220 from FIG. 2. These operations may map orphan unmapped regimens 106 through a mapping manager interface 110 such that when sufficient regimen data has accumulated over time, such orphan unmapped regimens may become mapped to, for example, a regimen from a reference library of cancer treatment regimens. This mapping manager interface 110 may be configured to receive manual mapping results 108 from, for example, human experts endeavoring to provide examples as input to a machine learning process executed by logic vault 104. By virtue of this interaction, logic vault 104 may adaptively refine and optimize regimen mapping through either supervised or unsupervised machine learning. Once the reference regimen list has been updated, the results may be relayed, via mapping manager interface 112 to database manager 114 such that database 116 becomes updated to remain current. This operation is reflected in step 222 of FIG. 2. When future regimen data arrives in source vault 102 from healthcare providers and data vendors, queries are submitted at the database 116 through database manager 114 to determine whether this regimen data has been previously mapped. If so, the regimen data will be identified with a flag as "pre-mapped" with a pre-assigned reference regimen identification (ID). This process allows for quicker flow and interpretation of treatment regimen data, as explained in further detail below.

Figure 2:
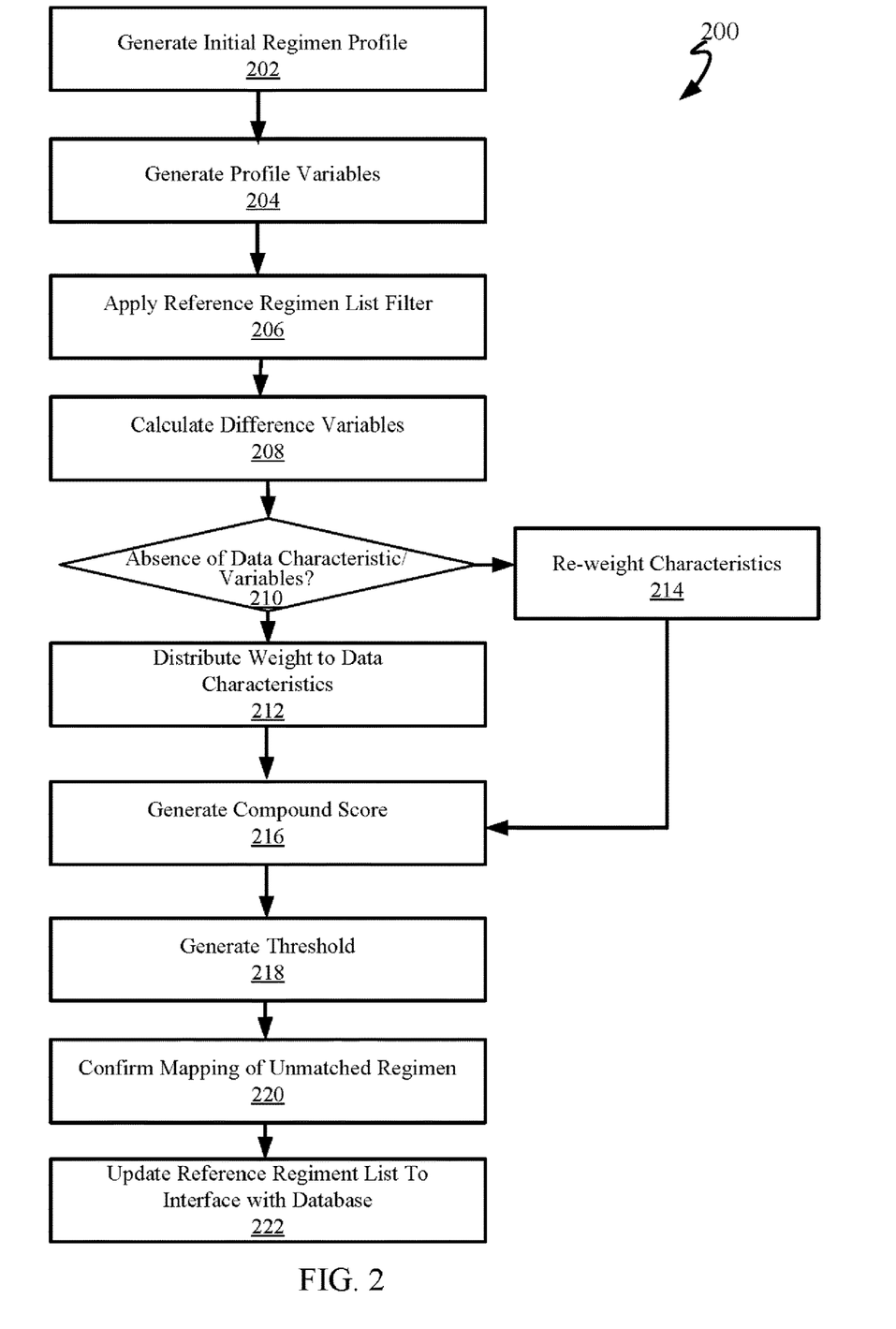
FIG. 2 illustrates an example of a process for regularizing cancer treatment data for systematic reporting and analysis.

Referring to both FIGS. 1 and 2, a processor in logic vault 104 may generate an initial regimen profile (202) based on each reported regimen data stored at source vault 102. During this process, the processor in logic vault 104 may transform healthcare provider (HCP) derived data into a multi-level hierarchy data structure for regimen mapping purposes. In some examples, supporting medication will also be recorded (e.g. medication to treat nausea) within a patient specific treatment plan; and yet this type of information may be removed from the unmatched regimen for mapping purposes as it does not define a regimen or indication for oncology treatment. In the case where generics are listed in the unmatched regimen, looser matching criteria may be subsequently applied where the drug class of the unmatched regimen drug name will be considered as a potential match against the list for reference regimens, even if the exact generic brand drug cannot be identified in the reference regimen list. Meanwhile, stricter criteria may be subsequently applied for branded drug name matching for cases where branded drugs are listed in the unmatched regimen. In these cases, a drug class match cannot be considered as a potential match but rather the reference regimen needs to contain the same name of the branded drug (or the names of the active ingredient) identified in the unmatched regimen to constitute a complete and exact match.

Figure 3:
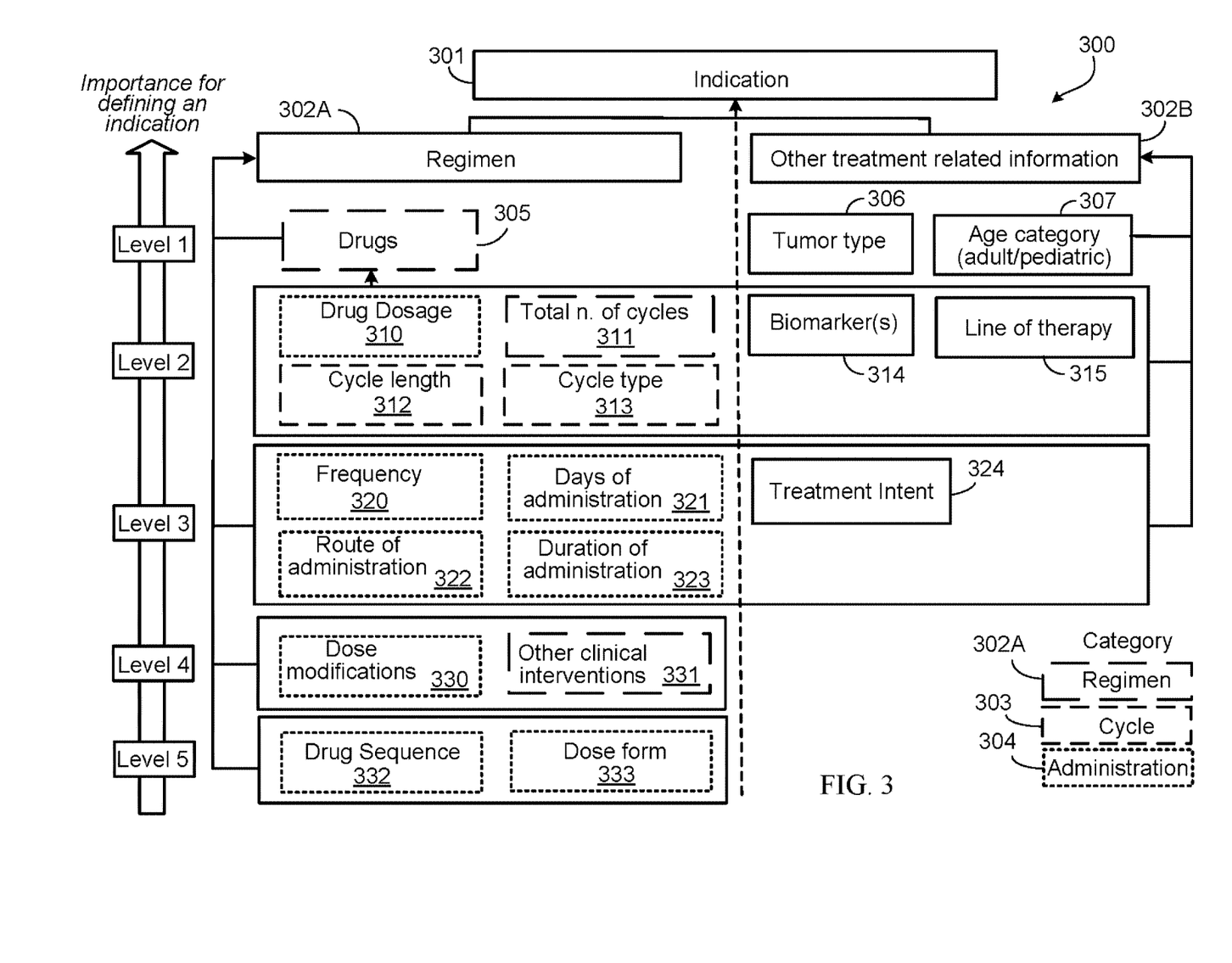
FIG. 3 illustrates an example of tiered data structure with data characteristics at various levels.

Further referring to FIG. 3, an example of the hierarchical layers of regimen profile is illustrated. Here, each indication 301 may refer to a particular oncological condition. For example, the indication may describe the organ impairment, morphological status, and line of therapy for which the drug is licensed for use. Regimen 302A is a top-level structure that parallels other treatment related information 302B. Cycle 303 is a mid-level structure that captures cycles of treatment, each cycle may encompass various characteristics. Administration 304 is a bottom-level structure in this hierarchy, which captures the characteristics of each administration of pharmaceuticals in a given cycle. Each structure may encompass data characteristics at various levels that signify an importance in defining an indication and drive the associated weighting in regimen mapping algorithm. In the example shown in FIG. 3, regimen 302A may encompass drugs 305 at level 1 of the importance ladder, total number of cycles 311 at level 2 of the importance ladder, and other clinical interventions 331 at level 4 of the importance ladder. While level 1 through level 5 are referred to in the example of FIG. 3, the levels may be alternatively numbered. For example, level 1 may be instead referred to as level E, level 2 may be instead referred to as level D, etc. In general, data characteristics higher up in the importance ladder weigh more than those located lower in this importance ladder.

Cycle 303 may include cycle length 312 and cycle type 313, both of which are located at level 2 of the importance ladder. Administration 304 may encompass drug dosage 310 at level 2 of the importance ladder; frequency 320, days of administration 321, route of administration 322, and duration of administration 323 at level 3 of the importance ladder; dose modification 330 at level 4 of the importance ladder; and drug sequence 332, dose form 333 at level 5 of the importance ladder. Meanwhile, other treatment related information 302B encompasses tumor type 306 and age category 307 at level 1 of the importance ladder; biomarker 314, line of therapy 315 at level 2 of the importance ladder; and treatment intent 324 at level 3 of the importance ladder. Such information may also be used as, for example, tie breakers when comparison of the main information leads to an impasse. Generally, the availability of treatment related information 302B depends on local oncology center practice.

Referring back to FIGS. 1 and 2, the processor at logic vault 104 may then generate profile variables (204) for each regimen. During this step, the processor at logic vault 104 may inspect the presence of regimen related characteristics to determine whether gaps exists for regimen related characteristics; and if so, the processor at logic vault 104 may raise an appropriate flag. This step of flagging data gaps will also be beneficial in determining the impact of the missing data characteristics and indicate the number of calculated variables that this omission may impact. In the event that a significant number of data gaps or a significant number of calculated variables cannot be calculated, data capture and quality improvement that are site-specific may be readdressed. On the other hand, these unmatched regimens may remain unmapped and may remain temporarily stored in the data warehouse 102 until additional information is provided.

For unmatched regimens that pass the initial screening, the next step includes the processor at logic vault 104 applying a reference regimen list filter (206). At this stage, the data characteristic used from the unmatched regimen is a name of a drug or drugs, which may correspond to a variable under drugs 305 in FIG. 3. A number of filters may be applied at this stage so that an unmatched regimen can be passed through to compare against a shortlisted number of reference regimens (contained in the consolidated list of guidelines, an example of which is known as Core Regimen Reference List (CRRL)) which are more promising than others for matching.

The branded and generic drugs listed in the unmatched filter may be used to cross reference with the reference regimen list. It is possible that an exact match may be generated between drug brand/generic name(s) described in the unmatched regimen and a number of regimens listed in the example of the CRRL. Where only generic drugs are listed in the unmatched regimen, a search through the reference regimen list can allow for an exact match of the generic name contained in the reference regimen list. Alternatively, if an exact match cannot be located in the combination of generic drug names, a class match of the given generic drugs in the reference regimen list can be applied to pass the list through the first filter.

In some instances, the number of drugs included in the unmatched regimen versus the number of drugs listed in the reference regimen list may indicate the degree of match and will be considered when applying the above filters. There may be instances where the unmatched regimen reports a given number of branded products but the reference list produces outputs with regimens containing greater or fewer number of drugs listed. In such instances, if the search results contain one or all of the exact drug names (branded), the mismatch in the total number of drugs listed may not exclude the given reference regimen from being considered. For example, an unmatched regimen may report four (4) branded drugs. A search may be conducted through the reference regimen list seeking shortlisted reference regimens using the four (4) brand names of drugs. A number of results returned may include a potential reference list match that lists a greater number of drugs in the reference list in comparison to the unmatched regimen. For example, this reference list may list five (5) drugs instead of four (4) (including three (3) exact brand name matches and two (2) branded products not listed in the unmatched regimen). In this instance, this reference regimen would still be considered as a potential match and would not be excluded. In other words, the number of drugs listed in an unmatched regimen does not dictate whether reference regimens should be ruled out. However, a quantitative measure can be applied to determine the degree of distance between the unmatched regimen and reference regimens. Reference regimens such as these remain as shortlisted regimen and will undergo the remaining steps.

Table 1 below provides a working example of how the number of drugs listed in an unmatched regimen versus the number of drugs found in the reference regimen list can be used to quantitatively generate a degree of match. As illustrated, potential matches A, B and D are determined as lower priority while potential C is determined the closest potential match. Here, matches (A) and (D) are not excluded but the low level matching is considered as a factor when identifying the overall weighting of unmatched regimen versus the shortlisted references.

TABLE 1

| Potential Reference match | no. of drugs in unmatched regimen | No. of overlapping drugs | No. of drugs in Reference | % match | Order of Match |
|---|---|---|---|---|---|
| A | 4 | 2 | 4 | 2/4 = 50% | =3 |
| B | 4 | 4 | 6 | 4/6 = 66% | 2 |

TABLE 1-continued

| Potential Reference match | no. of drugs in unmatched regimen | No. of overlapping drugs | No. of drugs in Reference | % match | Order of Match |
|---|---|---|---|---|---|
| C | 4 | 3 | 4 | 3/4 = 75% | 1 |
| D | 4 | 3 | 6 | 3/6 = 50% | =3 |

The process may then proceed to calculate differences between variables (208) to allow for a quantitative comparison of regimen related data characteristic values reported in the unmatched regimen against the reference regimen list. Each data characteristic listed in FIG. 3 can be reviewed systematically so that a number of calculations may be applied to the available data to generate quantitative values to reflect the degree of match between unmatched regimen and the potential reference regimen list at the level of data characteristics. These data characteristics are split into either regimen 302A (which is a data structure that includes treatment regimen-related data characteristics) or other treatment related information 302B, as illustrated in FIG. 3.

The regimen related data characteristics 302A are also split into tiers to reflect an initial view of the level of importance in defining indication. The level at which the data characteristics are distributed suggests the level of importance/requirement to supporting the regimen mapping needs. The hierarchy of FIG. 3 is only an example. Data models may evolve over time and data characteristic may shift across tiers as healthcare provider data arrives. The extent of data gaps may be identified and the regimen mapping algorithm may be developed. In practice, given the likelihood of data gaps in other treatment related information (e.g., a biomarker, a line of therapy etc.) 302B, the treatment regimen related data characteristics from regimen 302A may be more advantageously used in the regimen mapping algorithm to map treatment plans and local reference regimens to the reference regimen list.

In one embodiment, each data characteristics from FIG. 3 are compared to capture the degree of match at various levels. For example, the comparison may capture diagnostic information that include primary tumor, stage and histology of the primary tumor, and tumor mutation and expression. The comparison may also capture treatment plans that include intent of the treatment, components of the regimen/protocol, dosage and frequency information, and all product components for combination or multi-product regimens. In some instances, the comparison may further capture interruptions to treatment plan that provides context on the duration of therapy with information on likely treatment discontinuities. For example, the unmatched regimen can include portions of a treatment plan that can be patient specific and can vary among institutions. In these instances, the treatment plan may be implemented through some phases but not all phases. The unmatched regimen may also include trial and error rounds that deviate from an original treatment plan. Here, the reference regimen refers to a protocol of treatment which can cover a template regimen.

Some calculations may generate binary scores. In some cases, data characteristics such as drug dose form, route of administration and dose modification will generate qualitative values instead of quantitative values. For comparison between an unmatched regimen and a reference regimen list, some calculations may be attributed to a binary score depending on the level of match or mismatch.

Other calculations may generate range bounded real scores to reflect a degree of match. In particular, data characteristics with quantitative values may be compared between an unmatched regimen and a reference regimen list to arrive at a concluding real value score (ranging between 0 and 1, where 0 equates to a mismatch whilst 1 equates to a match). In this approach, positive and negative numbers are treated symmetrically. This approach imparts a quantitative perspective on the degree of match for a given data characteristics calculated variable. To confine the output of calculated variables with a range between 0 and 1, when calculated variables yield negative scores, the absolute value may be considered and the negative prefix may be de-prioritised. This approach of symmetry between positive and numbers does not compromise the overall result of identifying the degree of match between unmatched regimen and reference regimen list. In this approach, the unmatched regimen data values may be considered as the common denominator. When mean, mode, and median variables are calculated, a denominator may allow for relative comparison between the characteristics of the unmatched regimen instead of a peer set comparison. Where required, specific data characteristics may be used from the unmatched regimen as the common denominator instead of using the reference regimen. This approach may measure the degree of distance between unmatched regimen and each individual reference regimen in a consistent manner without skewing the results pending the earlier matching criteria applied.

For regimen mapping purposes, the data characteristics are further sub-dived into a level corresponding to regimen 302A, a level corresponding to cycle 303 and a level corresponding to administration 304 to support the hierarchy of data tables of reference regimens. As illustrated in FIG. 3, fourteen (14) data characteristics may be grouped at the level corresponding to regimen 302A, the level corresponding to cycle 303 and the level corresponding to administration 304. In some implementations, a series of calculated variables may be generated for each of the data characteristics to yield a high degree of mutual exclusivity as well as a high level of distinction. In some cases, one or more calculated variable(s) may be listed for a given data characteristic to account for multiple aspects of that data characteristic and the complexities of comparing specific components of a given regimen. These calculated variables may have been developed in a manner to account for the potential difference between unmatched regimen and reference regimen list and allow for a quantitative and fair comparison.

Further referring to FIG. 3, each drug name characteristic under drug 305 may be compared between the unmatched regimen (having its cocktail mixture) and each reference regimen in the reference list. The comparison of the unmatched regimen with a reference regimen may yield a score based on the sum of each drug name comparison over the total number of drugs in the unmatched regimen as per below, where N is the total number of drugs in the cocktail mixture and Comparison_i refers to the $i^{th}$ comparison of drug names in the cocktail mix.

$$\frac{\sum_{i=1}^{N} \text{Comparison\_i}}{N}$$

In the series of comparisons, branded drug names may entail an exact match yielding either a hit or a miss. Generic drug names may include a partial match, for example, when a similar drug from the same class has been used in the reference regimen.

The number of drugs may also be compared in multiple dimensions. In one example, the distance in the number of drugs between the unmatched regimen and the reference regimen may be determined according to the following formula:

$$1 - \frac{(a-b)}{sa},$$

where a is the number of drugs in the unmatched regimen and b is the number of drugs in the reference regimen, and e is the total number of drugs.

In another example, an additional binary score can be provided when comparing the total number of drugs listed in the unmatched regimen versus the reference regimen. Depending on the number of drugs listed in the comparison between unmatched regimen and the reference regimen, a real number value of 1 or 0 could be assigned. When the unmatched regimen and reference regimen display the same number of drug, this comparison may yield a value of 1. When the reference regimen displays more or less number of drugs in comparison to unmatched regimen, the comparison may be assigned a real number value of 0.

At the level corresponding to regimen 302A, a number of comparisons may be computed in a variety of aspects. In some instances, the total number of cycles (313) may be compared between an unmatched regimen and a reference regimen in three dimensions. Beyond the total number of cycles there are other characteristics of cycles within a regimen. For example, while the total number of cycles may be the same between the unmatched and reference, the number of days per cycle may vary and may be factored in analysis for comparison in these instances. For example, the total number of days across all cycles for the unmatched regimen and for the reference regimen may be calculated. A real number between 0 and 1, depending on the distance between the reference regimen and the unmatched regimen in terms of total number of days, may be assigned. Similar to the calculation under the number of drugs, the relative distance in the number of cycles between the unmatched regimen and a reference regimen results can be used to identify the closest degree of match near to 1 and the furthest degree of match towards 0. In one illustration, the number of cycles between the unmatched regimen and each reference regimen is compared.

At this level corresponding to regimen 302A, other clinical interventions (331) may be compared as another aspect. This comparison may entail a categorical match/mismatch. For example, if there is a direct categorical match between an unmatched regimen and a reference regimen, this comparison may yield 1. Otherwise, it may yield 0. In some implementations, an indirect categorical match may yield 0.5. In this case, an indirect categorical match may refer to a partial match.

At the level corresponding to cycle 303, which is the middle level in the data structure hierarchy in FIG. 3, a number of aspects may be compared. Cycle length (312) may be compared in terms of average number of days per cycle and variations of number of days per cycle. Each cycle may have a different number of days. The average number of days can be calculated for each reference regimen match such that a comparison of the mean durations between the unmatched regimen and each reference regimen match can be made. Where each cycle length varies, a comparison could be made in the delta number of days per cycle to differentiate the level of match per each reference regimen match. In one instance, the sum of the absolute number of the delta for each cycle is divided over the total of minimum cycles. Cycle type (313) may also entail a categorical comparison of each cycle type as well as the cumulative number of cycle types. Cycles may come in the form of a loading cycle, a maintenance cycle, etc. As a categorical match, the result of each comparison may be binary. Each binary result from each cycle comparison may be combined. Meanwhile, the number of cycle categories from the unmatched regimen may be compared with that from each reference regimen.

At the level corresponding to administration 304, which is the bottom level in the data structure hierarchy in FIG. 3, a number of aspects may be compared. Drug dosage (310) may also be compared in terms of mode dose basis, average dose basis per administration per drug, and average dose basis per administration per branded drug. While some regimens may entail repeated cycles, the dose used may vary for each cycle. Comparing the most frequently used dose per drug across the entire regimen may yield more insight than comparing each individual dose for drug in each cycle. Given the potential variance in drug doses and number of cycles, an average value may allow for closer quantitative matching between the unmatched regimen and each reference regimen. The average may be performed for those branded drugs as such drugs tend to be less accessible (or more expensive) than generics.

Drug sequence (332) may be compared as well at this level corresponding to administration 304. The sequence of drugs across all cycles may be compared. When there are only minor variations beyond Cycle 1 which plateau in later cycles, the sequence of drugs can be compared at the median cycle level which is likely to be most consistent. The comparison values for each cycle may be combined to generate a compound reading. In some instances, the comparison per cycle may be generate a binary readout for branded drugs. For generics, the readout may take fractional values when the drugs are from the same class.

The frequency (320) may also be compared at this level corresponding to administration 304. In this case, the mean number of administrations per drug per cycle may be compared to account for drug form, and route of administration form. The comparison results from all cycles may be combined.

The days of administration (321) also may be compared at this level corresponding to administration 304. In some instances, the average number of administration days per cycle can be calculated on the basis that drug forms match in the unmatched regimen and each reference regimen. For example, a biased result may be generated if an oral drug (with higher frequency of administration) is compared to IV (intravenous) administration. In this example, a robust comparison could be made to determine the average number of days of admin per cycle. In some cases, the median (or mean) days from the start and end of each cycle can be calculated for each cycle and averaged for the entire regimen. This may account for the potential differences in cycle durations; and the unmatched regimen and each reference regimen can be assessed independently.

Duration of administration (323) may include mode duration per drug throughout the regimen (per drug form). This approach identifies the most common duration of administration per drug across the regimen. Thus, this result may reveal more salient features in the unmatched regimen and each reference regimen. For example, in the unmatched regimen, a particular drug may be infused at a specific dose level for two hours. In comparison, a reference regimen may list this particular drug at this specific dose for infusion that lasts four hours. This calculation could be further split to exclude generics and only compare the branded drugs.

Route of administration (322) is another feature subject to comparison. For each drug, the most common route of administration could be determined at cycle level (independent of drugs) and compared. A binary score can then be applied depending on the mode match or mis-match. For example, a direct match may yield a 1, an indirect match for a 0.5, and no match for 0. In this example, an indirect match can be a partial match. The sum of number of routes of administration per drug can be used to determine the similarities between the unmatched regimen and each reference regimen as routes of administration are normally dictated by the dosage. If the dosage were to differ significantly between the unmatched regimen and each reference regimen, the route of admin is unlikely to be the same or similar.

Drug form (333) may be another factor subject to comparison. This factor may include a comparison between the unmatched regimen and all possible reference regimen results in either a direct categorical match (score of 1) or no match (score of 0). This factor may further include the total number different dose forms between the unmatched regimen and all possible reference regimen by accounting for the sum of types of dose forms for each drug.

Dose modification (330) may be yet another factor subject to comparison. As a categorical match, each direct match yields a 1, an indirect for 0.5, and no match for 0.

The contributions from these factors at each level in the hierarchy shown in FIG. 3. Combining the contributions may include assigning appropriate weighting to each data characteristic. If a given data characteristic presents more than one calculated variable, the assigned weighting is split equally between the multiple calculated variables. This weighted approach has been applied respectively to data characteristics to reflect the degree of importance assigned to each data characteristic in defining a regimen.

With specific reference to FIG. 2, the unmatched regimen may be missing certain data characteristics or certain data fields of a particular data characteristic. When this is determined to be the case, the list of weights may be re-arranged to account for the missing variables (214). In some cases, the re-arrangement may be done via respective distribution of the available percentage to data characteristics where those initially represent an initial higher weighting will receive a greater distribution. In some cases when more than one calculated variable is listed for a data characteristic but all cannot be exercised due to incomplete or missing data, the associated weighting will be omitted instead of re-distributed to the remaining calculated variables within a data characteristic. Inclusion of calculated variable weightings that represent missing data can give rise to bias and therefore should not be included. Alternatively to (214) above, when no data variable is missing, the list of weights may be distributed to all data characteristics (212).

While an initial list of weights may be assigned to each data characteristics, the list of weights may undergo refinement through, for example, a machine learning process that adapts the weight assignment to be more consistent with expert input. Indeed, a number of approaches will also be employed to refine the calculated variables, the assigned weighting of data characteristics and the overall regimen mapping process. Input may be solicited from various third-party entities, professional organizations, or standard committees. Feedback from these expert inputs (rather than a single input source) may be utilized to update the proposed calculations and weighting. In some instances, a Bayesian statistical approach will be employed to build and execute the regimen mapping algorithm. In particular, Markov Chain Monte Carlo (MCMC) methods may be incorporated to compute large hierarchical models that require integrations over hundreds or even thousands of unknown parameters.

Once re-weighted, the new weighting of each data characteristic is multiplied with the results of each calculated variable score. This will generate a number of scores which are then aggregated to create a compound score (216). This compound score determines the degree of comparison between the unmatched regimen and a particular reference regimen.

When comparing compounding scores, multiple matches may be present and the differences between the respective compound scores (for regimen matching) are difficult to discern. Several approaches may be taken to generate a threshold level (218). A simple approach may rank the raw compound scores and the highest percentage match reference regimen may be identified as the closest match. The shortcomings of this approach is that the risk of ambiguity may lead to a sub-optimal decision. To mitigate the risk of ambiguity, patient characteristic may be reviewed as a tie breaker. Additional review can be conducted on the similar regimens and an associated relationship may be developed with one identified as a parent regimen. Such information may be further reconciled with the reference regimen list.

Once compound scores are generated and compared for each reference regimen (vis a vis the unmatched regimen), the choice threshold is applied and the prevailing reference regimen may be identified as the closest match to the unmatched regimen (220). In some instances, the corresponding compound scores from a number of data records are comparable and close to each other, thereby forming a group of contenders. In these cases, when the corresponding compound scores from more than a threshold number of data records are close to each other, for example, within a particular margin, then, the respective weight to each data characteristic in the hierarchy may be re-distributed. In other words, a stirring event can be applied in these cases to cause a re-distribution of weights so that the number of close contenders may be reduced. Here, the compounding score may confirm the implementation of comparison at all levels of the hierarchy.

Subsequently, the reference regimen list may be updated; and this mapping is fed back to database 116 through database manager 114. When future data arrives from healthcare providers and data vendors, queries are submitted at the database 116 through database manage 114 to determine whether this data has been previously mapped. If so, the data will be identified with a flag as "pre-mapped" with a pre-assigned reference regimen ID provided by the reference data store, for example, the CRRL. This process allows for quicker flow and interpretation of data.

In oncology, a regimen is a regulated course of medical treatment that consists of one or more drugs administrated over a period of time. Components of a standard regimen are modified based on the patient's age, weight, concomitant medication and overall well-being to generate a patient specific treatment plan. In practice, local clinicians use different names to refer to the same course of treatment. In the UK, for example, more than 20,000 different regimen names have been submitted, where some can be categorized, others are likely to be a variant of a common reference regimen and therefore significantly difficult to categorize. Unlike any other reference sources (e.g., $10^{th}$ revision of the International Statistical Classification of Diseases and Related Health Problems (ICD) of the World Health Organization), no standardized regimen lists are available either within a developed country or at an international level as a reference for comparison. In the UK, for example, the Systemic Anti-Cancer Therapy dataset (SACT) collects data from inconsistent sources and reports to the public on the use of the regimen. What is more, each local institution (e.g., a healthcare provider practitioner) may have its own local description of data elements for regimens and treatment plans. These sources of irregularity underscore the need for a standard reference list to facilitate mapping. Some implementations drive automated processing using the proposed algorithmic design to reconcile differing regimens across healthcare provider sites into a single reference using a consolidated list of regimens. Implementations disclosed herein may standardize regimen and treatment plan information so that healthcare providers and pharmaceutical companies can derive comparable analytics on oncology product use based on such information. The strategic importance for the claimed invention lies in its ability to rapidly facilitate comparable analysis on the complex and varied regimen and treatment plan structures used in local oncology practice across regions, countries and system types.

Figure 4:
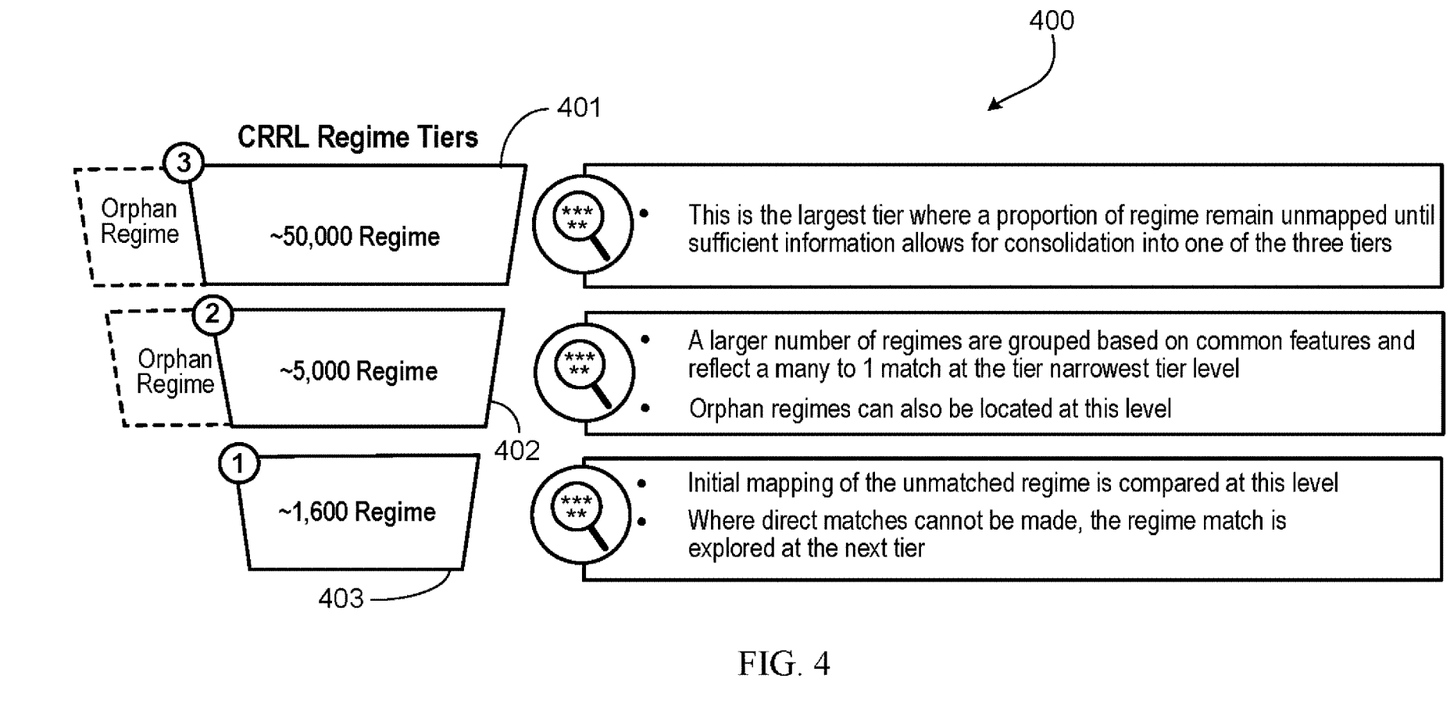
FIG. 4 illustrates an example of a multi-tier reference regimen list.

The disclosure may facilitate the consolidation of large sets of regimens and treatment plans. As illustrated by the example 400 in FIG. 4, the first tier 401 includes a large set of regimens where a proportion of the regimens remain unmapped until further information becomes available. At tier 402, a large number of regimens are grouped based on common features and reflect a many-to-one match at this level. As indicated, the total number of regimens become reduced. At tier 403, an initial mapping of the unmatched regimen may be derived that include a narrow set of, for example, about 1600 or fewer reference regimens. When direct matches cannot be made at this tier, further potential matches may be explored at upper tiers, such as tier 402 where a larger number of regimen are grouped.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A method comprising:
    parsing, based on a data structure hierarchy, a first data record that represents a first regimen for a disease, wherein the data structure hierarchy indicates a hierarchy for data records in a database, wherein the first data record has been encoded into a set of multi-tier characteristics, wherein each level of the set of multi-tier characteristics represents a respective trait of a treatment to a disease for a de-identified patient,
    based on parsing the first data record and in response to determining that the first regimen is mapped in the database, providing a second regimen of a prevailing data record in the database as a match for the first regimen, and
    based on parsing the first data record and in response to determining that the first regimen is not mapped in the database, obtaining a score indicative of a degree of match between the first regimen and the second regimen.

2. The method of claim 1, further comprising:
    benchmarking the first regimen based on an efficacy of the second regimen.

3. The method of claim 1, further comprising:
    recording treatment data during a course of the first regimen; and comparing the treatment data during the course of the first regimen with the prevailing data record.

4. The method of claim 3, further comprising:
based on comparing the treatment data with the prevailing data record, refining a set of weights to the set of multi-tier data characteristics.

5. The method of claim 1, wherein obtaining the score comprises applying a set of weights to the set of multi-tier data characteristics of the data structure hierarchy, wherein each weight in the set of weights is applied to a corresponding data characteristic of the set of multi-tier data characteristics.

6. The method of claim 5, further comprising:
identifying, based on applying the set of weights to the set of multi-tier data characteristics, the prevailing data record in the database.

7. The method of claim 5, further comprising:
in response to determining that a data characteristic of the data structure hierarchy is absent from the first data record, flagging the data characteristic as missing.

8. The method of claim 1, wherein the score indicative of a degree of match is based on comparing a first score and a second score, wherein the first score is based on the set of multi-tier data characteristics encoded from the first data record, and the second score is based on a second set of multi-tier data characteristics encoded from the prevailing data record.

9. A computer system comprising one or more processors, wherein the one or more processors are configured to perform operations of:
parsing, based on a data structure hierarchy, a first data record that represents a first regimen for a disease, wherein the data structure hierarchy indicates a hierarchy for data records in a database, wherein the first data record has been encoded into a set of multi-tier characteristics, wherein each level of the set of multi-tier characteristics represents a respective trait of a treatment to a disease for a de-identified patient,
based on parsing the first data record and in response to determining that the first regimen is mapped in the database, providing a second regimen of a prevailing data record in the database as a match for the first regimen, and
based on parsing the first data record and in response to determining that the first regimen is not mapped in the database, obtaining a score indicative of a degree of match between the first regimen and the second regimen.

10. The computer system of claim 9, further comprising:
benchmarking the first regimen based on an efficacy of the second regimen.

11. The computer system of claim 9, further comprising:
recording treatment data during a course of the first regimen; and
comparing the treatment data during the course of the first regimen with the prevailing data record.

12. The computer system of claim 11, further comprising:
based on comparing the treatment data with the prevailing data record, refining a set of weights to the set of multi-tier data characteristics.

13. The computer system of claim 9, wherein obtaining the score comprises applying a set of weights to the set of multi-tier data characteristics, wherein each weight in the set of weights is applied to a corresponding data characteristic of the set of multi-tier data characteristics.

14. The computer system of claim 13, further comprising:
identifying, based on applying the set of weights to the set of multi-tier data characteristics, the prevailing data record in the database.

15. The computer system of claim 13, further comprising:
in response to determining that a data characteristic of the data structure hierarchy is absent from the first data record, flagging the data characteristic as missing.

16. The computer system of claim 9, wherein the score indicative of a degree of match is based on comparing a first score and a second score, wherein the first score is based on the set of multi-tier data characteristics encoded from the first data record, and the second score is based on a second set of multi-tier data characteristics encoded from the prevailing data record.

17. A non-transitory computer-readable medium, comprising software instructions, that when executed by a computer, cause the computer to execute operations comprising:
parsing, based on a data structure hierarchy, a first data record that represents a first regimen for a disease, wherein the data structure hierarchy indicates a hierarchy for data records in a database, wherein the first data record has been encoded into a set of multi-tier characteristics, wherein each level of the set of multi-tier characteristics represents a respective trait of a treatment to a disease for a de-identified patient,
based on parsing the first data record and in response to determining that the first regimen is mapped in the database, providing a second regimen of a prevailing data record in the database as a match for the first regimen, and
based on parsing the first data record and in response to determining that the first regimen is not mapped in the database, obtaining a score indicative of a degree of match between the first regimen and the second regimen.

18. The non-transitory computer-readable medium of claim 17, wherein the operations further comprise:
benchmarking the first regimen based on an efficacy of the second regimen.

19. The non-transitory computer-readable medium of claim 17, wherein the operations further comprise:
recording treatment data during a course of the first regimen; and
comparing the treatment data during the course of the first regimen with the prevailing data record.

20. The non-transitory computer-readable medium of claim 19, wherein the operations further comprise:
based on comparing the treatment data with the prevailing data record, refining a set of weights to the set of multi-tier data characteristics.

* * * * *